United States Patent [19]

Bollag et al.

[11] 4,225,527

[45] Sep. 30, 1980

[54] POLYENE COMPOUNDS

[75] Inventors: Werner Bollag, Basel; Rudolf Rüegg, Bottmingen; Gottlieb Ryser, Basel, all of Switzerland

[73] Assignee: Hoffmann-La Roche Inc., Nutley, N.J.

[21] Appl. No.: 861,085

[22] Filed: Dec. 15, 1977

[30] Foreign Application Priority Data

Dec. 20, 1976 [AT] Austria .................................. 9444/76
Oct. 11, 1977 [CH] Switzerland ....................... 12388/77

[51] Int. Cl.³ .................................................. C11C 3/00
[52] U.S. Cl. ..................................... 260/408; 260/404; 260/413; 424/308; 424/318; 424/324; 424/340; 568/654; 568/11; 568/437
[58] Field of Search ........................... 424/308; 260/408

[56] References Cited

U.S. PATENT DOCUMENTS

| 3,781,314 | 12/1973 | Bollag et al. | 260/410.9 |
| 3,845,089 | 10/1974 | Henrick | 260/410.9 |
| 3,931,257 | 1/1976 | Pawson | 260/408 |
| 3,950,418 | 4/1976 | Bollag et al. | 260/557 R |
| 4,054,589 | 10/1977 | Bollag et al. | 568/649 |

FOREIGN PATENT DOCUMENTS

| 752927 | 7/1970 | Belgium . |
| 752928 | 7/1970 | Belgium . |
| 752929 | 7/1970 | Belgium . |
| 762344 | 2/1971 | Belgium . |
| 813002 | 3/1974 | Belgium . |
| 819117 | 2/1975 | Belgium . |
| 833784 | 3/1976 | Belgium . |
| 3539/71 | 6/1971 | South Africa . |

*Primary Examiner*—Allen J. Robinson
*Attorney, Agent, or Firm*—Jon S. Saxe; Bernard S. Leon; George W. Johnston

[57] ABSTRACT

Novel 9-(halo-substituted phenyl)-3,7-dimethyl-nona-2,4,6,8-tetraene derivatives useful in treating dermatological conditions.

3 Claims, No Drawings

POLYENE COMPOUNDS

SUMMARY OF THE INVENTION

This invention is directed to novel polyene compounds of the formula:

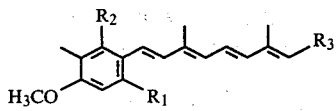

wherein $R_1$ and $R_2$ each are chlorine or bromine and $R_3$ is hydroxymethyl, alkoxymethyl, carboxyl, alkoxycarbonyl, mono(lower alkyl)carbamoyl or di(lower alkyl)carbamoyl,
and salts thereof, which are useful in treating dermatological conditions.

These polyene compounds are produced by treating novel compounds of the formula:

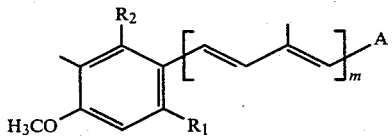

with novel compounds of the formula:

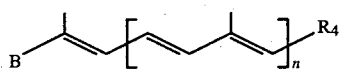

wherein $R_1$ and $R_2$ are defined above, m is zero when n is 1 or m is 1 when n is zero, one of A and B is formyl and the other is triarylphosphoniummethyl of the formula $-CH_2-P[X]_3^\oplus Y^\ominus$; X is aryl and Y is the anion of an organic or inorganic acid, and $R_4$ is alkoxymethyl, carboxyl, alkoxycarbonyl, mono(lower alkyl)carbamoyl or di(lower alkyl)carbamoyl when B is formyl, or $R_4$ is carboxyl, alkoxycarbonyl, mono(lower alkyl)carbamoyl or di(lower alkyl)carbamoyl when B is triarylphosphoniummethyl.

DETAILED DESCRIPTION OF THE INVENTION

The present invention is concerned with polyene compounds represented by the formula:

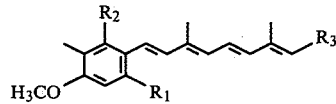

wherein $R_1$ and $R_2$ each are chlorine or bromine and $R_3$ is hydroxymethyl, alkoxymethyl, carboxyl, alkoxycarbonyl, mono(lower alkyl)carbamoyl or di(lower alkyl)carbamoyl,
and salts thereof.

The alkoxy groups of the aforementioned alkoxymethyl and alkoxycarbonyl substituents preferably contain 1 to 6 carbon atoms. These alkoxy groups can be straight-chain or branched-chain such as methoxy, ethoxy or isopropoxy. Higher alkoxy groups containing 7 to 20 carbon atoms are also suitable, especially cetyloxy. The lower alkyl groups of the aforementioned mono(lower alkyl)carbamoyl and di(lower alkyl)carbamoyl groups are straight-chain or branched-chained (e.g., methyl, ethyl or isopropyl). Examples of mono(lower alkyl)carbamoyl and di(lower alkyl)carbamoyl are methylcarbamoyl, ethylcarbamoyl and diethylcarbamoyl.

Examples of polyene compounds of formula I are:
9-(2,6-dichloro-4-methoxy-5-methyl-phenyl)-3,7-dimethyl-nona-2,4,6,8-tetraen-1-oic acid
9-(2,6-dichloro-4-methoxy-5-methyl-phenyl)-3,7-dimethyl-nona-2,4,6,8-tetraen-1-oic acid ethyl ester,
9-(2,6-dibromo-4-methoxy-5-methyl-phenyl)-3,7-dimethyl-nona-2,4,6,8-tetraen-1-oic acid ethyl ester,
9-(2,6-dichloro-4-methoxy-5-methyl-phenyl)-3,7-dimethyl-nona-2,4,6,8-tetraen-1-oic acid ethylamide,
9-(2,6-dichloro-4-methoxy-5-methyl-phenyl)-3,7-dimethyl-nona-2,4,6,8-tetraen-1-ol and
9-(2,6-dichloro-4-methoxy-5-methyl-phenyl)-3,7-dimethyl-nona-2,4,6,8-tetraene-1-methyl ether.

According to the process of the present invention, the polyene compounds of formula I and salts thereof are produced by reacting compounds of the formula:

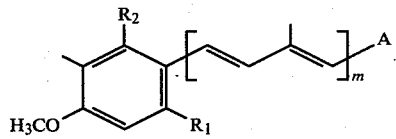

with compounds of the formula:

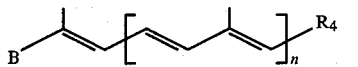

wherein $R_1$ and $R_2$ are defined above, m is zero when n is 1 or m is 1 when n is zero, one of A and B is formyl and the other is triarylphosphoniummethyl of the formula $-CH_2-P[X]_3^\oplus Y^\ominus$; X is aryl and Y is the anion of an organic or inorganic acid, and $R_4$ is alkoxymethyl, carboxyl, alkoxycarbonyl, mono(lower alkyl)carbamoyl or di(lower alkyl)carbamoyl when B is formyl, or $R_4$ is carboxyl, alkoxycarbonyl, mono(lower alkyl)carbamoyl or di(lower alkyl)carbamoyl when B is triarylphosphoniummethyl.

If desired, the resulting carboxylic acid can be converted to a salt of formula I, or a carboxylic acid ester of formula I or an amide of formula I. The carboxylic acid ester of formula I then can be converted to a carboxylic acid of formula I or an amide of formula I. Additionally, the resulting carboxylic acid or carboxylic acid ester of formula I can be converted to the corresponding alcohol of formula I which in turn can be esterfied.

The aryl groups (denoted by X) of the above trialkylphosphoniummethyl substituent having the formula $-CH_2-P[X]_3^\oplus Y^\ominus$ include all generally known aryl groups and especially mononuclear aryl groups such as phenyl, (lower alkyl)-phenyl or (lower alkoxy)-phenyl such as tolyl, xylyl, mesityl and p-methoxyphenyl. The inorganic acid anions (denoted by Y) of the above triarylphosphoniummethyl group are preferably chloride, bromide, iodide or hydrosulphate anions, and the preferred organic acid anion (denoted by Y) is the tosyloxy anion.

Certain of the compounds of formula II are novel and can be formed by processes which are described below.

Among the preferred novel compounds of formula II are compounds of the formula:

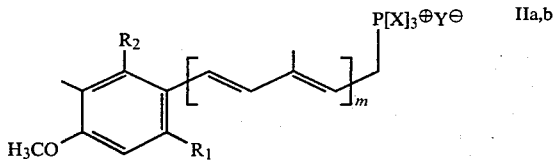

wherein $R_1$ and $R_2$ each are chlorine or bromine, $R_3$ is a hydroxymethyl, alkoxymethyl, carboxyl, alkoxycarbonyl, mono(lower alkyl)carbamoyl or di(lower alkyl)carbamoyl and m is zero or 1.

Illustratively, compounds of formula II wherein m is zero and A is triarylphosphoniummethyl (IIa) are prepared by treating an appropriately substituted benzene with formaldehyde in the presence of a hydrohalic acid (e.g., concentrated hydrochloric acid), optionally in a solvent (especially glacial acetic acid). The resulting substituted benzyl halide corresponds to formula II in which m is zero and A is halomethyl (IIe). This benzyl halide is reacted in a known manner with a triarylphosphine in a solvent, preferably triphenylphosphine in toluene or benzene.

The appropriately substituted benzene may be prepared by methylation of a hydroxy group of phenol. For example, the phenol is reacted with a methyl halide (e.g., methyl iodine) or dimethyl sulphate in the presence of a base (e.g., potassium carbonate) and preferably a solvent (e.g., an alkanol such as methanol) to produce the desired substituted benzene.

Compounds of formula II wherein m is 1 and A is triarylphosphoniummethyl (IIb) illustratively are prepared by formylating an appropriately substituted benzene. For example, a formylating agent may act upon the substituted benzene in the presence of a Lewis acid. Typical non-limiting formylating agents are orthoformic acid ester, formyl chloride and dimethylformamide. Suitable non-inclusive Lewis acids are the halides of zinc, aluminium, titanium, tin and iron such as zinc chloride, aluminium trichloride, titanium tetrachloride, tin tetrachloride and iron trichloride, as well as the halides of inorganic and organic acids such as phosphorus oxychloride and methanesulphonyl chloride.

If the formylating agent is present in excess, the formylation may be carried out without a further solvent. However, it is preferred to formylate the substituted benzene in an inert solvent (e.g., nitrobenzene or a chlorinated hydrocarbon such as methylene chloride). The formylation can be effectuated at temperatures from 0° C. to the boiling point of the formylation mixture.

The resulting substituted benzaldehyde (IIc) can be converted in a known manner by condensation with acetone at an approximate temperature range of 0° C. to 30° C. in the presence of alkali (e.g., dilute aqueous sodium hydroxide) to a (substituted phenyl)-but-3-en-2-one. The latter can be transformed into a (substituted phenyl)-3-methyl-3-hydroxy-penta-4-en-1-yne in a known manner by an organometallic reaction (e.g., a Grignard reaction with the addition of acetylene). The resulting tertiary acetylenic carbinol can be partially hydrogenated in a known manner using a partially deactivated noble metal catalyst (Lindlar catalyst). The resulting tertiary ethylenic carbinol can be converted into the desired phosphonium salt of formula IIb defined earlier under allylic rearrangement by treatment with a triarylphosphine (especially triphenylphosphine) in the presence of a mineral acid (e.g., a hydrogen halide such as hydrogen chloride or hydrogen bromide, or sulfuric acid) and a solvent (e.g., benzene). Alternatively, the tertiary ethylenic carbinol can be halogenated to yield a halide of formula II in which m is 1 and A is halomethyl (IIf) and this halide can be converted into the above phosphonium salt of formula IIb by treatment with a triarylphosphine (e.g., triphenylphosphine).

Compounds of formula II in which m is zero and A is formyl (IIc) illustratively are prepared by formylating an appropriately substituted benzene by the procedure previously described. In this manner, the substituted benzaldehyde of formula IIc is obtained directly from the substituted benzene.

Compounds of formula II in which m is 1 and A is formyl (IId) illustratively are prepared by reacting the above described (substituted phenyl)-but-3-en-2-one with ethoxycarbonylmethylene-triphenylphosphorane under the conditions of a Wittig reaction. The resulting (substituted phenyl)-3-methyl-penta-2,4-dien-1-oic acid ethyl ester is subsequently reduced at less than room temperature by a mixed metal halide (especially lithium aluminum hydride) in an organic solvent (e.g., ether or tetrahydrofuran) to yield a (substituted phenyl)-3-methyl-penta-2,4-dien-1-ol. This alcohol is then oxidized to give the desired (substituted phenyl)-3-methyl-penta-2,4-dien-1-al of formula IId by treatment with an oxidizing agent (e.g., manganese dioxide in an organic solvent such as acetone or methylene chloride) at approximate temperatures of 0° C. to the boiling point of the oxidation mixture.

Certain of the compounds of formula III are novel and can be obtained by the following process.

Compounds of formula III in which n is zero and B is triarylphosphoniummethyl (IIIa) illustratively are prepared by reacting either 4-halo-3-methyl-crotonic acid, which may be esterified, or an etherified 4-halo-3-methyl-crotyl alcohol with a triarylphosphine in a solvent, preferably triphenylphosphine in toluene.

Compounds of formula III in which n is 1 and B is triarylphosphoniummethyl (IIIb) illustratively are prepared by reducing the formyl group of an aldehyde of formula III in which n is 1 and B is formyl (IIId) to the hydroxymethyl group using a metal hydride (e.g., sodium borohydride) in an alkanol (e.g., ethanol or isopropanol). The alcohol obtained can be halogenated by a customary halogenating agent (e.g., phosphorus oxychloride) and the resulting 8-halo-3,7-dimethyl-octa-2,4,6-triene-1-carboxylic acid corresponds to formula III wherein n is 1 and B is halomethyl (IIIf). This acid halide or a derivative thereof can be reacted with a triarylphosphine in a solvent, preferably with triphenylphosphine in toluene or benzene, to give the desired phosphonium salt of formula IIIb.

Compounds of formula III in which n is zero and B is formyl (IIIc) illustratively are prepared by oxidatively cleaving an optionally esterified tartaric acid (e.g., using lead tetraacetate at room temperature in an organic solvent such as benzene). The resulting glyoxalic acid derivative is condensed with propionaldehyde in a known manner, conveniently in the presence of an amine, at elevated temperatures of 60° C. to 110° C. with cleavage of water which yields the desired 3-formyl-crotonic acid derivative.

Compounds of formula III in which n is 1 and B is formyl (IIId) illustratively are prepared by allowing phosgene to act on 4,4-dimethoxy-3-methyl-but-1-en-3-ol at low temperatures (preferably at −10° C. to −20° C.) in the presence of a tertiary amine such as pyridine and condensing the resulting 2-formyl-4-chloro-but-2-ene under the conditions of a Wittig reaction with a 3-formyl-crotonic acid, which may be esterified, or with an esterified 3-formyl-crotyl alcohol to give the desired aldehyde of formula IIId.

To produce the polyene compounds of formula I, a phosphonium salt of formula IIa or IIb is reacted with an aldehyde of formula IIId or IIIc, or a phosphonium salt of formula IIIa or IIIb is reacted with an aldehyde of formula IId or IIc.

By a Wittig procedure, the above starting materials are reacted with one another in the presence of an acid-binding agent (e.g., an alkali metal alcoholate such as sodium methylate or an alkylene oxide which may be alkyl-substituted, especially ethylene oxide or 1,2-butylene oxide), if desired in a solvent (e.g., a chlorinated hydrocarbon such as methylene chloride or dimethylformamide) approximately at room temperature to the boiling point of the reaction mixture.

It is sometimes convenient to carry out the Wittig reaction in situ, that is, without isolating the phosphonium salt starting material from the medium in which it is prepared.

A carboxylic acid of formula I can be converted in a known manner (e.g., by treatment with thionyl chloride, preferably in pyridine) into an acid chloride which can be converted into an ester by reaction with an alkanol or into an amide by reaction with an alkylamine.

A carboxylic acid ester of formula I can be hydrolyzed to a carboxylic acid of formula I in a known manner. For example, the carboxylic acid ester is treated with an alkali, especially aqueous-alcoholic sodium hydroxide or potassium hydroxide approximately at room temperature to the boiling point of the mixture. The resulting carboxylic acid can then be amidated via an acid halide as described previously. Alternatively, a carboxylic acid ester can be directly amidated as will be described hereinafter.

A carboxylic acid ester of formula I can be transformed directly into a corresponding alkyl-substituted amide by treatment with an alkyl-substituted lithium amide. This treatment preferably is effectuated at room temperature.

A carboxylic acid or a carboxylic acid ester of formula I can be reduced to a corresponding alcohol of formula I in a known manner. The reduction is advantageously effectuated by a metal hydride or alkyl metal hydride in an inert solvent. Suitable nonlimiting hydrides are mixed metal hydrides such as lithium aluminium hydride and bis(methoxy-ethyleneoxy)-sodium aluminium hydride. Suitable non-inclusive solvents are ether (e.g., diethylether) tetrahydrofuran or dioxan when lithium aluminium hydride is used and ether, hexane, benzene or toluene when diisobutylaluminium hydride or bis(methoxy-ethyleneoxy)-sodium aluminium hydride is utilized.

Illustratively, an alcohol of formula I can be etherified with an alkyl halide (e.g., ethyl iodide) in the presence of a base (preferably sodium hydride) in an organic solvent (e.g., dioxan, tetrahydrofuran, 1,2-dimethoxyethane or dimethylformamide), or in the presence of an alkali metal alcoholate in an alkanol, at temperatures from about 0° C. to about room temperature.

A carboxylic acid of formula I forms salts with bases, especially with alkali metal hydroxides and preferably with sodium hydroxide or potassium hydroxide.

The polyene compounds of formula I can occur as cis/trans mixtures which may be separated in a known manner into the cis and trans components or they may be isomerized in a known manner to all-trans compounds.

The polyene compounds of the present invention are pharmacodynamically valuable.

The polyene compounds of formula I are suitable for the topical and systemic thereapy of acne, psoriasis and other dermatoses accompanied by an increased or pathologically altered cornification, as well as for the treatment of inflammatory and allergic dermatological conditions.

Advantageously, the toxicity exhibited by the present polyene compounds is slight. For example, when 9-(2,6-dichloro-4-methoxy-5-methyl-phenyl)-3,7-dimethyl-nona-2,4,6,8-tetraen-1-oic acid ethyl ester is administered intraperitoneally to mice weighing 30 g. in a daily dosage of 6 mg./kg., hypervitaminosis-A is not evident even after 14 days (total of 10 administration days).

The first indications of even a slight hypervitaminosis-A, which manifests itself in a weight decrease of 20%, a moderate hair loss and a slight flaking of the skin, appears after 14 days (total of 10 administration days) in the mice which were administered a daily dosage of 12 mg./kg.

The inhibiting activity of the present polyene compounds is significant. In a papilloma test, tumors induced by dimethylbenzanthracene and croton oil regress after treatment with the polyene compounds of the present invention. The diameter of the papilloma in the course of two weeks after the intraperitoneal administration of 9-(2,6-dichloro-4-methoxy-5-methyl-phenyl)-3,7-dimethyl-nona-2,4,6,8-tetraen-1-oic acid ethyl ester decreases as follows:

85% at a dosage of 25 mg./kg./week;
59% at a dosage of 12 mg./kg./week; and
42% at a dosage of 6 mg./kg./week.

Following oral administration of 9-(2,6-dichloro-4-methoxy-5-methyl-phenyl)-3,7-dimethyl-nona-2,4,6,8-tetraen-1-oic acid ethyl ester, the diameter of the induced tumors decreases in the course of 2 weeks (5 individual dosages/week) as follows:

72% with a dosage of 25 mg. (5×5 mg.)/kg./week;
62% with a dosage of 12.5 mg. (5×2.5 mg.)/kg./week;
43% with a dosage of 6.25 mg. (5×1.25 mg.)/kg./week; and
41% with a dosage of 3.0 mg. (5×0.60 mg.)/kg./week.

The polyene compounds of the present invention accordingly are useful as medicaments; for example, in the form of pharmaceutical preparations containing the present polyene compounds and a compatible pharmaceutical carrier material.

Pharmaceutical preparations for systemic administration can be illustratively prepared by adding a compound of formula I as the active ingredient to conventional non-toxic, inert, solid or liquid carriers.

The pharmaceutical preparations can be administered enterally or parenterally. Suitable pharmaceutical preparations for enteral administration illustratively are tablets, capsules, dragees, syrups, suspensions, solutions and suppositories. Suitable pharmaceutical preparations for parenteral administration include infusion or injection solutions.

The dosages in which the present polyene compounds are administered can be varied according to the mode and route of administration and according to the requirements of the patient. For example, amounts of ca 1 to ca 30 mg. of the polyene compounds can be administered daily in a single dosage or divided dosages. Capsules containing ca 1 mg. to ca 10 mg. of the active polyene ingredient are a preferred form of administration.

The pharmaceutical preparations can contain inert or pharmacodynamically active additives. Tablets or granules, for example, can contain a series of binders, fillers, carrier materials or diluents. Liquid preparations illustratively can take the form of sterile water-miscible solutions. Capsules can contain a filler or thickener. Furthermore, flavor-improving additives, preservatives, stabilizers, wetting agents or emulsifiers, salts for varying the osmotic pressure, buffers, and other adjuvants can also be present in the pharmaceutical preparations.

The aforementioned carrier materials and diluents can be organic or inorganic substances such as water, gelatin, lactose, starch, magnesium stearate, talc, gum arabic, polyalkyleneglycols and the like. It is, of course, a prerequisite that all adjuvants used in the preparation of the pharmaceutical preparations be non-toxic.

For topical administration, the present polyene compounds are conveniently prepared as ointments, tinctures, creams, solutions, lotions, sprays, suspensions and the like. Ointments, creams and solutions are preferred. The pharmaceutical preparations for topical administration can be prepared by mixing the present polyene compound as the active ingredient with non-toxic inert solids or liquid carriers which are customarily utilized in such preparations.

When prepared as solutions, the weight concentrations of the polyene active ingredients are ca 0.01% to ca 0.3%, preferably 0.02% to 0.1%. When prepared in the form of ointments or creams, the weight concentrations of the polyene compounds are ca 0.05% to ca 5%, preferably ca 0.05% to ca 1%.

If desired, an antioxidant (e.g., tocopherol, N-methyl-γ-tocopheramine, butylated hydroxyanisole or butylated hydroxytoluene) can be present in the pharmaceutical preparations.

The following non-limiting Examples illustrate the present invention. All temperatures are in degrees centigrade and the ether utilized is diethylether.

In the Examples, vol.% denotes ml in 100 ml and % w/vol. denotes g in 100 ml.

EXAMPLE 1

100 g. of 2,6-dichloro-4-methoxy-5-methyl-benzyl-triphenylphosphonium chloride, prepared from 52 g. of 2,6-dichloro-4-methoxy-3-methyl-benzyl chloride and 57 g. of triphenylphosphine, are treated with 42 g. of 7-formyl-3-methyl-octa-2,4,6-trien-1-oic acid ethyl ester. After the addition of 120 ml. of 1,2-butylene oxide, the resulting mixture is heated to 80°–85° C. for 4 hours while stirring. The mixture is diluted with toluene/hexane (1:1 parts by volume) and exhaustively extracted with methanol/water (60:40 parts by volume). The resulting solution is evaporated under reduced pressure. The oily residue is purified by adsorption on silica gel using toluene for the elution. 9-(2,6-dichloro-4-methoxy-3-methyl-phenyl)-3,7-dimethyl-nona-2,4,6,8-tetraen-1-oic acid ethyl ester is obtained from the eluate and melts at 100°–101° C. after recrystallization from benzene/hexane (50:50 parts by volume).

EXAMPLE 2

The 2,6-dichloro-4-methoxy-5-methyl-benzyl-triphenylphosphonium chloride used as the starting material of Example 1 is prepared as follows:

103.0 g. of 2-nitro-4,6-dichloro-toluene are dissolved in 500 ml. of ethyl acetate. After the addition of 2 ml. of Raney-nickel, the resulting solution is hydrogenated at room temperature and under normal pressure. The hydrogenation is interrupted after 43 liters of hydrogen have been taken up. The catalyst is filtered off while gasing with carbon dioxide and is washed with ethanol. The combined filtrates are evaporated under reduced pressure. After rectification, the residual 2-amino-4,6-dichloro-toluene boils at 85° C./0.4 mmHg.

While stirring and cooling, 67 g. of 2-amino-4,6,-dichloro-toluene are introduced gradually into 250 ml. of concentrated sulfuric acid. The temperature of the mixture rises to 60° C. The mixture is cooled to 0° C. by the gradual addition of 750 g. of ice and is then treated dropwise within 3 hours with a solution of 26.4 g. of sodium nitrite in 80 ml. of water. The resulting mixture is stirred for 90 minutes at 0° C. to 10° C. and subsequently filtered. The filtrate is subjected to steam distillation with the dropwise addition of 600 ml. of sulfuric acid (50 vol. %) and the distillate is extracted three times with 1000 ml. of methylene chloride. The methylene chloride extract is dried over sodium sulphate and evaporated. After recrystallization from hexane, the residual 2-hydroxy-4,6-dichloro-toluene melts at 51°–52° C.

400 ml. of methanol and 85.5 ml. of dimethyl sulphate are added to 79 g. of 2-hydroxy-4,6-dichloro-toluene and the resulting mixture is stirred and treated dropwise with 256.5 ml. of potassium hydroxide (25% w/vol.). The resulting mixture which heats up to boiling during this dropwise addition, is stirred under reflux for 4 hours and subsequently evaporated. The residue is taken up in 600 ml. of water. The aqueous solution is extracted three times with 600 ml. of ether. The ether extract is washed neutral with water, dried over sodium sulphate and evaporated under reduced pressure. After rectification, the residual 2-methoxy-4,6-dichloro-toluene boils at 69°–70° C./0.1 mmHg.

68.0 g. of 2-methoxy-4,6-dichloro-toluene are mixed with 235 ml. of acetic acid, 446 ml. of hydrochloric acid (37% w/vol.) and 107 ml. of formaldehyde (35%) The resulting mixture is stirred at 70° C. for 3 hours and, after cooling, introduced into 2000 ml. of water. The aqueous solution is extracted three times with 1000 ml. of methylene chloride.

The methylene chloride extract is washed three times with 1000 ml. of water, dried over sodium sulphate and evaporated. The residual 2,6-dichloro-4-methoxy-5-methyl-benzyl chloride is purified by adsorption on silica gel using low boiling petroleum ether for the elution. After recrystallization from hexane, the resulting 2,6-dichloro-4-methoxy-5-methyl-benzyl chloride melts at 84°–85° C.

This resulting chloride is subsequently reacted with triphenylphosphine to yield 2,6-dichloro-4-methoxy-5-methyl-benzyl-triphenylphosphonium chloride.

EXAMPLE 3

By the procedure described in Example 1, 2,6-dibromo-4-methoxy-5-methyl-benzyl-triphenylphosphonium chloride is reacted with 7-formyl-3-methyl-octa-2,4,6-trien-1-oic acid ethyl ester. The resulting compound is 9-(2,6-dibromo-4-methoxy-5-methyl-phenyl)-3,7-dimethyl-nona-2,4,6,8-tetraen-1-oic acid ethyl ester (m.p. 101°–102° C.).

EXAMPLE 4

The 2,6-dibromo-4-methoxy-5-methyl-benzyl-triphenylphosphonium chloride used as the starting material of Example 3 is prepared in a manner analogous to that described in Example 2 from 2-nitro-4,6-dibromo-toluene (m.p. 64°–65° C.) via 2-amino-4,6-dibromo-toluene (m.p. 85° C./0.4 mmHg), 2-hydroxy-4,6-dibromo-toluene (m.p. 101°–102° C.) and 2,6-dibromo-4-methoxy-5-methyl-benzyl chloride.

EXAMPLE 5

52 g. of 1-ethoxycarbonyl-2,6-dimethyl-hepta-1,3,5-triene-7-triphenylphosphonium bromide are dissolved in 220 ml. of dimethylformamide. After the addition of 21.9 g. of 2,6-dichloro-4-methoxy-5-methyl-benzaldehyde, the resulting solution is cooled to 10° C.; treated dropwise with a solution of 2.4 g. of sodium in 60 ml. of absolute ethanol; and subsequently stirred at room temperature for 12 hours. The resulting mixture is diluted with toluene/hexane (1:1) and extracted with methanol/water (60:40 parts by volume.) The solution is then evaporated under reduced pressure. After purification by adsorption on silica gel using toluene for the elution and recrystallization from benzene/hexane (50:50 parts by volume), the residual 9-(2,6-dichloro-4-methoxy-5-methyl-phenyl)-3,7-dimethyl-nona-2,4,6,8-tetraen-1-oic acid ethyl ester melts at 99°–100° C.

EXAMPLE 6

The 2,6-dichloro-4-methoxy-5-methyl-benzenaldehyde (m.p. 110°–111° C.) used as the starting material of Example 5 is prepared from 3,5-dichloro-2-methyl-phenol (m.p. 51°–52° C.) via 3,5-dichloro-2-methyl-anisole (b.p. 76° C./0.3 mmHg; $n_D^{24}=1.5538$) and 2,6-dichloro-4-methoxy-5-methyl-benzyl chloride (m.p. 85°–86° C.).

EXAMPLE 7

27 g. of 5-(2,6-dichloro-4-methoxy-5-methyl-phenyl)-3-methyl-penta-2,4-diene-1-triphenylphosphonium bromide are introduced under nitrogen into 100 ml. of dimethylformamide and, while cooling at 5°–10° C. treated within 20 minutes with 1.75 g. of a suspension of sodium hydride (50%) in mineral oil. The resulting mixture is stirred at about 10° C. for 1 hour; then treated dropwise at 5°–8° C. with 7.1 g. of 3-formyl-crotonic acid ethyl ester; heated to 65° C. for 2 hours; subsequently introduced into ice-water; and, after the addition of sodium chloride, extracted with 100 ml. of hexane. The extract is washed with methanol/water (6:4 parts by volume), dried over sodium sulphate and evaporated under reduced pressure. After recrystallization from benzene/hexane (50:50 parts by volume), the residual 5-(2,6-dichloro-4-methoxy-5-methyl-phenyl)-3,7-dimethyl-nona-2,4,6,8-tetraen-1-oic acid ethyl ester melts at 100°–101° C.

EXAMPLE 8

The 5-(2,6-dichloro-4-methoxy-5-methyl-phenyl)-3-methyl-penta-2,4-diene-1-triphenylphosphonium bromide used as the starting material of Example 7 is prepared from 3,5-dichloro-2-methyl-phenol (m.p. 51°–52° C.) via 3,5-dichloro-2-methyl-anisole (b.p. 76° C./0.32 mmHg; $n_D^{24}=1.5538$) 3,5-dichloro-2-methyl-p-anisaldehyde (m.p. 110°–111° C.), 4-(2,6-dichloro-4-methoxy-5-methyl-phenyl)-but-3-en-2-one (m.p. 55°–56° C.), 5-(2,6-dichloro-4-methoxy-5-methyl-phenyl)-3-methyl-3-hydroxy-pent-4-en-1-yne ($n_D^{24}=1.5718$) and 5-(2,6-dichloro-4-methoxy-5-methyl-phenyl)-3-methyl-penta-2,4-dien-1-ol ($n_D^{23}=1.5661$).

EXAMPLE 9

42 g. of 9-(2,6-dichloro-4-methoxy-5-methyl-phenyl)-3,7-dimethyl-nona-2,4,6,8-tetraen-1-oic acid ethyl ester are dissolved in 750 ml. of ethanol. The solution is treated with 41 g. of potassium hydroxide in 63 ml. of water, heated to boiling under nitrogen for 30 minutes, cooled, introduced into water and acidified with hydrochloric acid. The precipitated 9-(2,6-dichloro-4-methoxy-5-methyl-phenyl)-3,7-dimethyl-nona-2,4,6,8-tetraen-1-oic acid melts at 252°–254° C.

EXAMPLE 10

15 g. of 9-(2,6dichloro-4-methoxy-5-methyl-phenyl)-3,7-dimethyl-nona-2,4,6,8-tetraen-1-oic acid are dissolved in 750 ml. of tetrahydrofuran. The resulting solution is treated with 2.64 ml. (0.7 m.) of phosphorus trichloride. After 12 hours, the resulting mixture is concentrated to half volume at 30° C. under reduced pressure and introduced dropwise at 0°–5° C. into a tetrahydrofuran solution containing 14.6 g. of ethylamine. The resulting mixture is stirred at room temperature for 1 hour, introduced into a saturated aqueous sodium chloride solution and extracted with methylene chloride. The extract is washed with an aqueous sodium chloride solution, dried and evaporated under reduced pressure. The residual 9-(2,6-dichloro-4-methoxy-5-methyl-phenyl)-3,7-dimethyl-nona-2,4,6,8-tetraen-1-oic acid ethylamide is purified by adsorption on silica gel using diethyl ether for the elution and after recrystallization from ethyl acetate melts at 128°–129° C.

EXAMPLE 11

13.8 g. of 9-(2,6-dichloro-4-methoxy-5-methyl-phenyl)-3,7-dimethyl-nona-2,4,6,8-tetraen-1-oic acid ethyl ester are dissolved in 170 ml. of toluene. The resulting solution is cooled under nitrogen while stirring and treated at 0°–2° C. with 80 ml. of a 20% solution of diisobutylaluminium hydride in toluene. The resulting mixture is stirred at 0° C. for 30 minutes, cautiously introduced into water and extracted with toluene. The toluene extract is washed several times with water, dried over sodium sulphate and evaporated under reduced pressure. The residual 9-(2,6-dichloro-4-methoxy-5-methyl-phenyl)-3,7-dimethyl-nona-2,4,6,8-tetraen-1-ol is purified by adsorption on silica gel using diethyl ether for the elution. This alcohol melts at 128°–129° C. after recrystallization from benzene.

EXAMPLE 12

8.1 g. of 9-(2,6-dichloro-4-methoxy-5-methyl-phenyl)-3,7-dimethyl-nona-2,4,6,8-tetraen-1-ol are dissolved in 100 ml. of tetrahydrofuran. After the addition of 10 g. of a sodium hydride/oil suspension which was washed with benzene at 0° C., the resulting solution is treated dropwise at 0°-2° C. with 10 ml. of methyl iodide. The mixture is stirred at 0° C. for 2 hours and then at room temperature for 12 hours, subsequently diluted with 200 ml. of toluene and cautiously introduced into water. The toluene phase is separated, washed neutral with water, dried over sodium sulphate and evaporated under reduced pressure. The residual 9-(2,6-dichloro-4-methoxy-5-methyl-phenyl)-3,7-dimethyl-nona-2,4,6,8-tetraene-1-methyl ether is purified by adsorption on silica gel using toluene for the elution. This resulting ether melts at 104°-105° C. after recrystallization for hexane.

EXAMPLE 13

15 g. of 9-(2,6-dichloro-4-methoxy-5-methyl-phenyl)-3,7-dimethyl-nona-2,4,6,8-tetraen-1-oic acid ethyl ester [cis/trans mixture (50:50 parts by volume)] are chromatographed on 1.5 kg. of silica gel (activity grade I) using hexane/toluene (80:20 parts by volume) for the elution. The 9-(2,6-dichloro-4-methoxy-5-methyl-phenyl)-3,7-dimethyl-nona-2-cis,4-trans,6-trans,8-trans-tetraen-1-oic acid ethyl ester, which can be isolated from the first runnings, melts at 108°-109° C. after recrystallization from hexane.

The following Examples illustrates typical pharmaceutical preparations containing the polyene compounds of the present invention.

EXAMPLE 14

A capsule composition contains the following ingredients:

| | |
|---|---|
| 9-(2,6-dichloro-4-methoxy-5-methyl-phenyl)-3,7-dimethyl-nona-2,4,6,8-tetraen-1-oic acid ethyl ester | 1 mg. |
| Wax mixture | 50.5 mg. |
| Vegetable oil | 98.0 mg. |
| Trisodium salt of ethylenediamine-tetraacetic acid | 0.5 mg. |
| Individual weight of one capsule | 150 mg. |
| Active ingredient content of one capsule | 1 mg |

EXAMPLE 15

An ointment containing 0.1% of active ingredient has the following composition:

| | |
|---|---|
| 9-(2,6-dichloro-4-methoxy-5-methyl-phenyl)-3,7-dimethyl-nona-2,4,6,8-tetraen-1-oic acid ethyl ester | 0.1 g. |
| Cetyl alcohol | 2.7 g. |
| Lanolin | 6.0 g. |
| Vaseline | 15.0 g. |
| Distilled water q.s. ad | 100.0 g. |

We claim:
1. A compound of the formula:

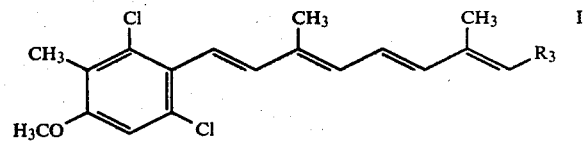

wherein $R_3$ is alkoxycarbonyl with its alkoxy moiety having 1 to 6 carbon atoms, or a salt thereof.

2. The polyene compound of claim 1 wherein said compound is 9-(2,6-dichloro-4-methoxy-5-methyl-phenyl)-3,7-dimethyl-nona-2,4,6,8-tetraen-1-oic acid ethyl ester.

3. The polyene compound of claim 1 wherein said compound is 9-(2,6-dichloro-4-methoxy-5-methyl-phenyl)-3,7-dimethyl-nona-2-cis,4-trans,6-trans,8-trans-tetraen-1-oic acid ethyl ester.

* * * * *